United States Patent
Wang et al.

(10) Patent No.: US 11,384,036 B2
(45) Date of Patent: Jul. 12, 2022

(54) METHOD FOR PREPARING AROMATIC HYDROCARBONS BY HYDROCRACKING POLYMER CONTAINING AROMATIC RING

(71) Applicant: East China University of Science and Technology, Shanghai (CN)

(72) Inventors: Yanqin Wang, Shanghai (CN); Yaxuan Jing, Shanghai (CN); Yong Guo, Shanghai (CN); Xiaohui Liu, Shanghai (CN); Ning Yan, Shanghai (CN)

(73) Assignee: East China University of Science and Technology, Shanghai (CN)

( * ) Notice: Subject to any disclaimer, the term of this patent is extended or adjusted under 35 U.S.C. 154(b) by 0 days.

(21) Appl. No.: 17/403,321

(22) Filed: Aug. 16, 2021

(65) Prior Publication Data
US 2022/0002216 A1 Jan. 6, 2022

(30) Foreign Application Priority Data
Jul. 3, 2020 (CN) .......................... 202010630920.7

(51) Int. Cl.
*C07C 4/06* (2006.01)
*C07C 1/32* (2006.01)
(Continued)

(52) U.S. Cl.
CPC .................. *C07C 4/06* (2013.01); *C07C 1/20* (2013.01); *C07C 1/322* (2013.01); *B09B 3/40* (2022.01); *C07C 2521/04* (2013.01); *C07C 2521/08* (2013.01); *C07C 2523/10* (2013.01); *C07C 2523/20* (2013.01); *C07C 2523/42* (2013.01);
(Continued)

(58) Field of Classification Search
CPC .. C07C 4/06; C07C 1/20; C07C 1/322; C07C 2521/04; C07C 2521/08; C07C 2523/10; C07C 2523/20; C07C 2523/42; C07C 2523/44; C07C 2523/46; C07C 2523/72; C07C 2523/745; C07C 2523/75;
(Continued)

(56) References Cited

U.S. PATENT DOCUMENTS 6,184,430 B1 * 2/2001 Venkatesh ............... C07C 5/226
585/750

* cited by examiner

*Primary Examiner* — Thuan D Dang
(74) *Attorney, Agent, or Firm* — Westbridge IP LLC

(57) ABSTRACT

Disclosed is a method for preparing aromatic hydrocarbons by hydrocracking a polymer containing aromatic rings, which includes reacting the polymer fragment with hydrogen under the action of a catalyst at a temperature of no more than 350° C.; separating a reaction product to obtain the aromatic hydrocarbons. The catalyst comprises a carrier and an active ingredient supported on the carrier, the active ingredient is at least one selected from Ru, Rh, Pt, Pd, Fe, Ni, Cu and Co, the carrier is at least one selected from metal oxide, phosphate, molecular sieve, $SiO_2$ and sulfonated carbon, the metal oxide is at least one selected from $Al_2O_3$, $Nb_2O_5$, $Nb_2O_5$—$Al_2O_3$, $Nb_2O_5$—$SiO_2$, $TiO_2$, $ZrO_2$, $CeO_2$ and $MoO_3$; the phosphate is at least one selected from $NbOPO_4$ and $ZrOPO_4$; and the molecule sieve is at least one selected from Nb-SBA-15, Nafion, H-ZSM-5, H-Beta and H-Y.

6 Claims, 1 Drawing Sheet

(51) Int. Cl.
  *C07C 1/20* (2006.01)
  *B09B 3/40* (2022.01)
(52) U.S. Cl.
  CPC ...... *C07C 2523/44* (2013.01); *C07C 2523/46* (2013.01); *C07C 2523/72* (2013.01); *C07C 2523/745* (2013.01); *C07C 2523/75* (2013.01); *C07C 2523/755* (2013.01)
(58) Field of Classification Search
  CPC . C07C 2523/755; B09B 3/40; B09B 2101/75; C08J 11/16; C08J 2367/02
  See application file for complete search history.

METHOD FOR PREPARING AROMATIC HYDROCARBONS BY HYDROCRACKING POLYMER CONTAINING AROMATIC RING

CROSS-REFERENCE TO RELATED APPLICATIONS

The present application claims priority of Chinese Patent Application 202010630920.7 entitled "Method for Preparing Aromatic Hydrocarbons by Hydrocracking Polymer Containing Aromatic Ring", filed on Jul. 3, 2020, the entire contents of which are incorporated herein by reference.

TECHNICAL FIELD

The present disclosure relates to industrial catalysis, in particular to a method for preparing aromatic hydrocarbons by hydrocracking a polymer containing aromatic rings.

BACKGROUND

Plastic pollution is one of the most serious environmental pollution, and plastics are mostly organic synthetic polymer materials. It is estimated that the global annual production of plastics has reached 334.83 million tons, but only 14% of them can be recycled due to technical problems. In the process of recycling, the yield of plastic needs to reach 30% before industrial production. At present, the main treatments of plastic recycling are combustion, decomposition, pyrolysis/cracking and the like. For the combustion treatment, toxic waste gas is often produced, and the product is complex; while for the decomposition treatment, the product is usually complex, the yield is low and the decomposition is incomplete; for the pyrolysis/cracking treatment, it usually requires high temperature of no less than 500° C., or it has low selectivity and low yield, it is difficult to separate the product, which do not possess the potential of industrialization. Therefore, it is necessary to develop a new strategy to recycle the polymers into high value-added chemicals with high selectivity.

SUMMARY

In view of this, the present disclosure provides a method for preparing aromatic hydrocarbons by hydrocracking a polymer containing aromatic rings, so as to solve the problems of complex product and low yield existing in the recycling of existing plastics.

According to some examples of the present disclosure, the method for preparing aromatic hydrocarbons by hydrocracking a polymer containing aromatic rings may include:

reacting the polymer containing aromatic rings dispersed in a solvent with hydrogen under the action of a catalyst at a temperature of no more than 350° C.;

separating a reaction product to obtain the aromatic hydrocarbons; wherein, the catalyst may include a carrier and an active ingredient supported on the carrier, the active ingredient may include at least one of Ru, Rh, Pt, Pd, Fe, Ni, Cu or Co, the carrier may include at least one of metal oxide, phosphate, molecule sieve, $SiO_2$ or sulfonated carbon, the metal oxide may include at least one of $Al_2O_3$, $Nb_2O_5$, $Nb_2O_5$—$Al_2O_3$, $Nb_2O_5$—$SiO_2$, $TiO_2$, $ZrO_2$, $CeO_2$ or $MoO_3$;

the phosphate may include at least one of $NbOPO_4$ or $ZrOPO_4$; and the molecule sieve may include at least one of Nb-SBA-15, Nafion, H-ZSM-5, H-Beta or H-Y.

There is a high demand for the selectivity of the cracking of benzene ring for preparing the aromatic hydrocarbons by hydrocracking the polymer containing aromatic rings. In order to obtain the aromatic hydrocarbons in high yield, proper catalyst is needed to high selectively break the C—O and C—C bonds connected with the benzene ring, but without a hydrogenation of the benzene ring. If the conventional catalyst has enough C—O and C—C bond breaking activity in the hydrogenation of the polymer containing aromatic rings, it is easy to also have the activity of the hydrogenation for the benzene ring, and it is difficult to have high selectivity for breaking the C—O and C—C bonds connected with the benzene ring. Therefore, highly selective catalytic break of the C—O and C—C bonds connected with benzene ring has a high demand for the catalyst.

In the present disclosure, through the synergistic effect of the metal and the carrier in catalyst, Lewis acid can activate the C—O bond with high selectivity, Bronsted acid can protonated the benzene ring, thus reducing the energy required for breaking the C—O and C—C bonds, and under the synergistic effect of appropriate hydrogenation sites, the C—O and C—C bonds connected with the benzene ring can be highly selectively broken, avoiding hydrogenation of the benzene ring and obtaining the aromatic hydrocarbons.

Therefore, the method of the present disclosure first has high selectivity, can selectively break the C—O and C—C bonds connected with the benzene ring in the polymer, and does not hydrogenate the benzene ring to obtain the aromatic hydrocarbons, which can be used as raw materials for the production of medicine, plastics, fiber, perfume, ink, etc., and has high value added. Secondly, the highest molar yield of the aromatic hydrocarbons can reach 85%, which has good industrial value.

BRIEF DESCRIPTION OF DRAWINGS

In order to more clearly explain the examples of the present disclosure or the technical solutions in the prior art, the following is a brief introduction to the drawings to be used in the description of the examples. It is obvious that the drawings described below are only some examples of the present disclosure. For those skilled in the art, without paying creative labor, they can also obtain other drawings from these drawings.

DETAILED DESCRIPTION OF THE EMBODIMENTS

In order to make the purpose, technical solutions, and advantages of the present disclosure clearer, the present disclosure is further described in detail below in combination with specific Examples and with reference to the accompanying drawings.

The inventor of the present disclosure notices in the long-term work of conversion treatment of the polymer containing aromatic rings that the polymer containing aromatic rings, such as polyethylene terephthalate-based, polyphenylene oxide-based, polycarbonate-based, polystyrene-based, polysulfone-based, polyphenylene sulfide-based, polyphenylacetylene-based and the like, are a high polymer formed by the connection of aromatic monomers through the C—O and C—C bonds. Based on this structural feature, if an efficient catalytic system can be developed to selectively break the C—O and C—C bonds and avoid the hydrogenation of the aromatic rings at the same time, monocyclic aromatic hydrocarbons with high selectivity can be prepared and an effective recycling of polymer waste plastics can be realized. However, there is no catalyst to achieve this challenging goal.

Without the carrier of any existing theory, the inventor of the present disclosure first proposes a method for preparing aromatic hydrocarbons by hydrocracking a polymer containing aromatic rings, and selects a metal supported-solid acid catalyst, the solid acid catalyst comprises a carrier and an active ingredient supported on the carrier, the active ingredient is at least one selected from Ru, Rh, Pt, Pd, Fe, Ni, Cu and Co, and the carrier is at least one selected from metal oxide, phosphate, molecular sieve, $SiO_2$ and sulfonated carbon. The metal supported-solid acid catalyst can break the C—O and C—C bonds in the polymer containing aromatic rings through selective hydrogenolysis, without hydrogenation of the aromatic ring, so as to prepare the aromatic hydrocarbons. The plastic compound waste can be efficiently catalyzed and converted at a temperature of no more than 350° C. through the method provided in the present disclosure, and the prepared aromatic hydrocarbons can be used as bulk chemicals or fuels, and the highest molar yield of the aromatic hydrocarbons can reach 85%.

Figure 1:
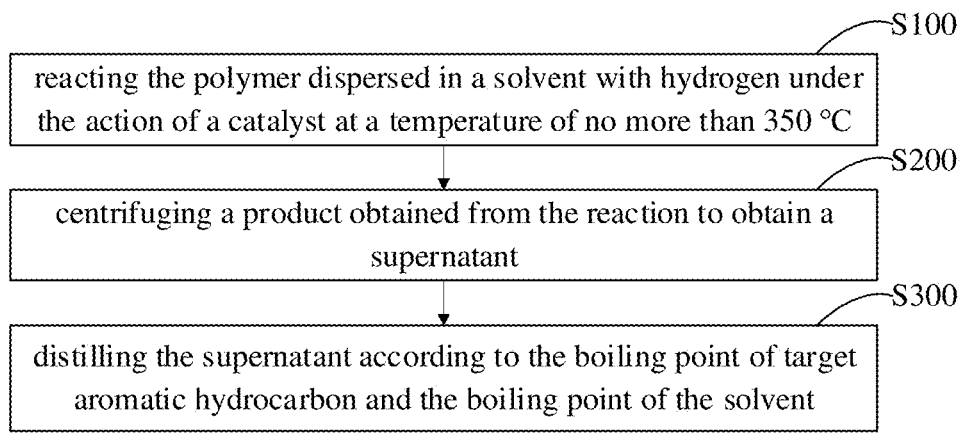
FIG. 1 shows a flow chart of preparing aromatic hydrocarbons by hydrocracking polymer waste according to some examples of the present disclosure.

Referring to FIG. 1, the method for preparing the aromatic hydrocarbons by hydrocracking the polymer may include:

In block S100, reacting the polymer dispersed in a solvent with hydrogen under the action of a catalyst at a temperature of no more than 350° C.

In block S200, centrifuging a product obtained from the reaction to obtain a supernatant.

In block S300, distilling the supernatant according to the boiling point of target aromatic hydrocarbons and the boiling point of the solvent, to obtain the aromatic hydrocarbons.

According to some examples of the present disclosure, before the step S100, the method may further include: crushing the polymer; and the crushed polymer is dispersed in a solvent.

In the above method, the polymer can be a single kind of polymer or a mixture of various kinds of polymers. For the mixture of various kinds of polymers, the mixing ratio can be any proportion, and the selective conversion can be realized under the same reaction conditions to prepare the aromatic hydrocarbons.

The polymer may be a polymer containing aromatic rings, which is at least one selected from polyethylene terephthalate, polyphenylene oxide, polycarbonate, polystyrene, polysulfone, polyphenylene sulfide and polyphenylacetylene.

According to some examples of the present disclosure, the polymer containing aromatic rings may include at least one of polyethylene terephthalate, polyphenylene oxide, polycarbonate or polystyrene.

Further, the polymer containing aromatic rings may include at least one selected from polycarbonate and polystyrene.

The polymer containing aromatic rings can be crushed to the extent of easy loading. For example, the particle size can be 10 mm.

The solvent may include at least one of cyclohexane, hexane, heptane, octane, dodecane, toluene, benzene, ethylbenzene, 1,4-dioxane or water.

In step S100, the mass ratio of the polymer containing aromatic rings to the catalyst is 0.1~100:1, the reaction temperature is 150~350° C., the hydrogen pressure is 0.1~10 MPa, the reaction time is 1~50 h. The mass concentration of the reactant is the mass percentage of the polymer containing aromatic rings to the solvent, which can be 0.1-100%.

The catalyst may include a carrier and an active ingredient supported on the carrier, and the active ingredient may include at least one of Ru, Fe, Ni, Cu or Co.

The carrier may be selected from metal oxide, phosphate, molecular sieve, $SiO_2$ or sulfonated carbon.

The metal oxide in the carrier may be selected from $Al_2O_3$, $Nb_2O_5$, $Nb_2O_5$—$Al_2O_3$, $Nb_2O_5$—$SiO_2$, $TiO_2$, $ZrO_2$, $CeO_2$ or $MoO_3$; the phosphate may be selected from $NbOPO_4$ or $ZrOPO_4$; and the molecule sieve may be selected from Nb-SBA-15, Nafion, H-ZSM-5, H-Beta or H-Y.

According to some examples of the present disclosure, the active ingredient may be Ru, and the carrier may include at least one of molecular sieve, an oxide of zirconium, an oxide of cerium, an oxide of niobium, a phosphate of niobium or molecular sieve of niobium, such as at least one selected from H-ZSM-5, $ZrO_2$, $CeO_2$, $Nb_2O_5$, $Nb_2O_5$—$Al_2O_3$, Nb-SBA-15, $Nb_2O_5$—$SiO_2$ and $NbOPO_4$.

Further, in the catalyst, the active ingredient may be Ru, and the carrier may include at least one of $Nb_2O_5$, $Nb_2O_5$—$Al_2O_3$, Nb-SBA-15, $Nb_2O_5$—$SiO_2$ or $NbOPO_4$.

Further, in the catalyst, the active ingredient may be Ru, and the carrier may include at least one of $Nb_2O_5$, $Nb_2O_5$—$Al_2O_3$, Nb-SBA-15 or $NbOPO_4$.

Further, in the catalyst, the active ingredient may be Ru, and the carrier may include at least one of $Nb_2O_5$, $Nb_2O_5$—$Al_2O_3$ or $NbOPO_4$.

Further, in the catalyst, the active ingredient may be Ru, and the carrier may include at least one of $Nb_2O_5$ or $NbOPO_4$.

Further, in the catalyst, the active ingredient may be Ru and the carrier may include $Nb_2O_5$.

According to some examples of the present disclosure, in the catalyst, the active ingredient may be Pd, and the carrier may include at least one of $Nb_2O_5$, $Nb_2O_5$—$Al_2O_3$, Nb-SBA-15, $Nb_2O_5$—$SiO_2$ or $NbOPO_4$.

Further, in the catalyst, the active ingredient may be Pd, and the carrier may include at least one of $Nb_2O_5$, $Nb_2O_5$—$Al_2O_3$, Nb-SBA-15 or $NbOPO_4$.

Further, in the catalyst, the active ingredient may be Pd, and the carrier may include at least one of Nb-SBA-15, $Nb_2O_5$—$Al_2O_3$ or $NbOPO_4$.

Further, in the catalyst, the active ingredient may be Pd, and the carrier may include at least one of Nb-SBA-15 or $Nb_2O_5$—$Al_2O_3$.

Further, in the catalyst, the active ingredient may be Pd and the carrier may include $Nb_2O_5$—$Al_2O_3$.

According to some examples of the present disclosure, the active ingredient may be Pt, and the carrier may include at least one of an oxide of aluminum, an oxide of cerium, an oxide of niobium, a phosphate of niobium or molecular sieve of niobium, such as at least one selected from $Al_2O_3$, $CeO_2$, $Nb_2O_5$, $Nb_2O_5$—$Al_2O_3$, Nb-SBA-15, $Nb_2O_5$—$SiO_2$ and $NbOPO_4$.

Further, in the catalyst, the active ingredient may be Pt, and the carrier may include at least one of $Nb_2O_5$, $Nb_2O_5$—$Al_2O_3$, Nb-SBA-15, $Nb_2O_5$—$SiO_2$ or $NbOPO_4$.

Further, in the catalyst, the active ingredient may be Pt, and the carrier may include at least one of $Nb_2O_5$—$SiO_2$, $Nb_2O_5$—$Al_2O_3$, NB-SBA-15 or $NbOPO_4$.

Further, in the catalyst, the active ingredient may be Pt, and the carrier may include at least one of $Nb_2O_5$—$Al_2O_3$, Nb-SBA-15 or $NbOPO_4$.

Further, in the catalyst, the active ingredient may be Pt, and the carrier may include at least one of $Nb_2O_5$—$Al_2O_3$ or Nb-SBA-15.

Further, in the catalyst, the active ingredient may be Pt and the carrier may include $Nb_2O_5$—$Al_2O_3$.

According to some examples of the present disclosure, the active ingredient may be Rh, and the carrier may include at least one of an oxide of aluminum, an oxide of cerium, an oxide of niobium, a phosphate of niobium or molecular sieve of niobium, such as at least one selected from $Al_2O_3$, $CeO_2$, $Nb_2O_5$, $Nb_2O_5$—$Al_2O_3$, Nb-SBA-15, $Nb_2O_5$—$SiO_2$ and $NbOPO_4$.

Further, in the catalyst, the active ingredient may be Rh, and the carrier may include at least one of $Nb_2O_5$, $Nb_2O_5$—$Al_2O_3$, Nb-SBA-15, $Nb_2O_5$—$SiO_2$ or $NbOPO_4$.

Further, in the catalyst, the active ingredient may be Rh, and the carrier may include at least one of $Nb_2O_5$, $Nb_2O_5$—$Al_2O_3$, Nb-SBA-15 or $Nb_2O_5$—$SiO_2$.

Further, in the catalyst, the active ingredient may be Rh, and the carrier may include at least one of $Nb_2O_5$, $Nb_2O_5$—$Al_2O_3$ or Nb-SBA-15.

Further, in the catalyst, the active ingredient may be Rh, and the carrier may include at least one of $Nb_2O_5$ or $Nb_2O_5$—$Al_2O_3$.

Further, in the catalyst, the active ingredient may be Rh and the carrier may include $Nb_2O_5$—$Al_2O_3$.

Further, in the catalyst, the active ingredient may be Ni, and the carrier may include at least one of $Nb_2O_5$, $Nb_2O_5$—$Al_2O_3$, Nb-SBA-15, $Nb_2O_5$—$SiO_2$ or $NbOPO_4$.

Further, in the catalyst, the active ingredient may be Ni, and the carrier may include at least one of $Nb_2O_5$—$SiO_2$, $Nb_2O_5$—$Al_2O_3$, Nb-SBA-15 or $NbOPO_4$.

Further, in the catalyst, the active ingredient may be Ni, and the carrier may include at least one of Nb-SBA-15, $Nb_2O_5$—$Al_2O_3$ or $NbOPO_4$.

Further, in the catalyst, the active ingredient may be Ni, and the carrier may include at least one of $Nb_2O_5$—$Al_2O_3$ or $NbOPO_4$.

Further, in the catalyst, the active ingredient may be Ni and the carrier may include $Nb_2O_5$—$Al_2O_3$.

Further, in the catalyst, the active ingredient may be Fe, and the carrier may include at least one of $Nb_2O_5$, $Nb_2O_5$—$Al_2O_3$, Nb-SBA-15, $Nb_2O_5$—$SiO_2$ or $NbOPO_4$.

Further, in the catalyst, the active ingredient may be Fe, and the carrier may include at least one of $Nb_2O_5$, $Nb_2O_5$—$Al_2O_3$, Nb-SBA-15 or $NbOPO_4$.

Further, in the catalyst, the active ingredient may be Fe, and the carrier may include at least one of $Nb_2O_5$, Nb-SBA-15 or $NbOPO_4$.

Further, in the catalyst, the active ingredient may be Fe, and the carrier may include at least one selected from Nb-SBA-15 or $NbOPO_4$.

Further, in the catalyst, the active ingredient may be Fe and the carrier may include Nb-SBA-15.

According to some examples of the present disclosure, the active ingredient may be Co, and the carrier may include at least one of molecular sieve, an oxide of zirconium, an oxide of cerium, an oxide of niobium, a phosphate of niobium or molecular sieve of niobium, specifically at least one selected from HZSM-5, $ZrO_2$, $CeO_2$, $Nb_2O_5$, $Nb_2O_5$—$Al_2O_3$, Nb-SBA-15, $Nb_2O_5$—$SiO_2$ or $NbOPO_4$.

Further, in the catalyst, the active ingredient may be Co, and the carrier may include at least one of $Nb_2O_5$, $Nb_2O_5$—$Al_2O_3$, Nb-SBA-15, $Nb_2O_5$—$SiO_2$ or $NbOPO_4$.

Further, in the catalyst, the active ingredient may be Co, and the carrier may include at least one of $Nb_2O_5$, $Nb_2O_5$—$SiO_2$, Nb-SBA-15 or $NbOPO_4$.

Further, in the catalyst, the active ingredient may be Co, and the carrier may include at least one of $Nb_2O_5$, $Nb_2O_5$—$SiO_2$ or $NbOPO_4$.

Further, in the catalyst, the active ingredient may be Co, and the carrier may include at least one of $Nb_2O_5$ or $Nb_2O_5$—$SiO_2$.

Further, in the catalyst, the active ingredient may be Co and the carrier may include $Nb_2O_5$—$SiO_2$.

According to some examples of the present disclosure, the active ingredient may be Cu, and the carrier may include at least one of molecular sieve, an oxide of zirconium, an oxide of cerium, an oxide of niobium, a phosphate of niobium or molecular sieve of niobium, specifically at least one selected from HZSM-5, $ZrO_2$, $CeO_2$, $Nb_2O_5$, $Nb_2O_5$—$Al_2O_3$, Nb-SBA-15, $Nb_2O_5$—$SiO_2$ or $NbOPO_4$.

Further, in the catalyst, the active ingredient may be Cu, and the carrier may include at least one of $Nb_2O_5$, $Nb_2O_5$—$Al_2O_3$, Nb-SBA-15, $Nb_2O_5$—$SiO_2$ or $NbOPO_4$.

Further, in the catalyst, the active ingredient may be Cu, and the carrier may include at least one of $Nb_2O_5$, $Nb_2O_5$—$SiO_2$, Nb-SBA-15 or $NbOPO_4$.

Further, in the catalyst, the active ingredient may be Cu, and the carrier may include at least one of $Nb_2O_5$, $Nb_2O_5$—$SiO_2$ or Nb-SBA-15.

Further, in the catalyst, the active ingredient may be Cu, and the carrier may include at least one of $Nb_2O_5$ or $Nb_2O_5$—$SiO_2$.

Further, in the catalyst, the active ingredient may be Cu and the carrier may include $Nb_2O_5$—$SiO_2$.

In step S200, the product obtained from the reaction is separated by centrifugation, the precipitate is used as a catalyst, and the aromatic hydrocarbons are in the supernatant. The obtained catalyst can be calcined at a temperature such as 400° C., to remove the coking/carbon deposition on the surface of the catalyst, so that the catalyst can be regenerated, the service life of the catalyst can be prolonged, the cost of the catalyst can be reduced and the use efficiency of the catalyst can be improved.

In step S300, the supernatant after centrifugation is taken, according to the boiling point of the aromatic hydrocarbons and the boiling point of the solvent, the centrifuged supernatant is separated in an order from low boiling point to high boiling point. The aromatic hydrocarbons can be at least one selected from benzene, toluene, p-xylene, m-xylene, ethylbenzene, o-xylene, cumene, indene and substituted indene.

Figure 2:
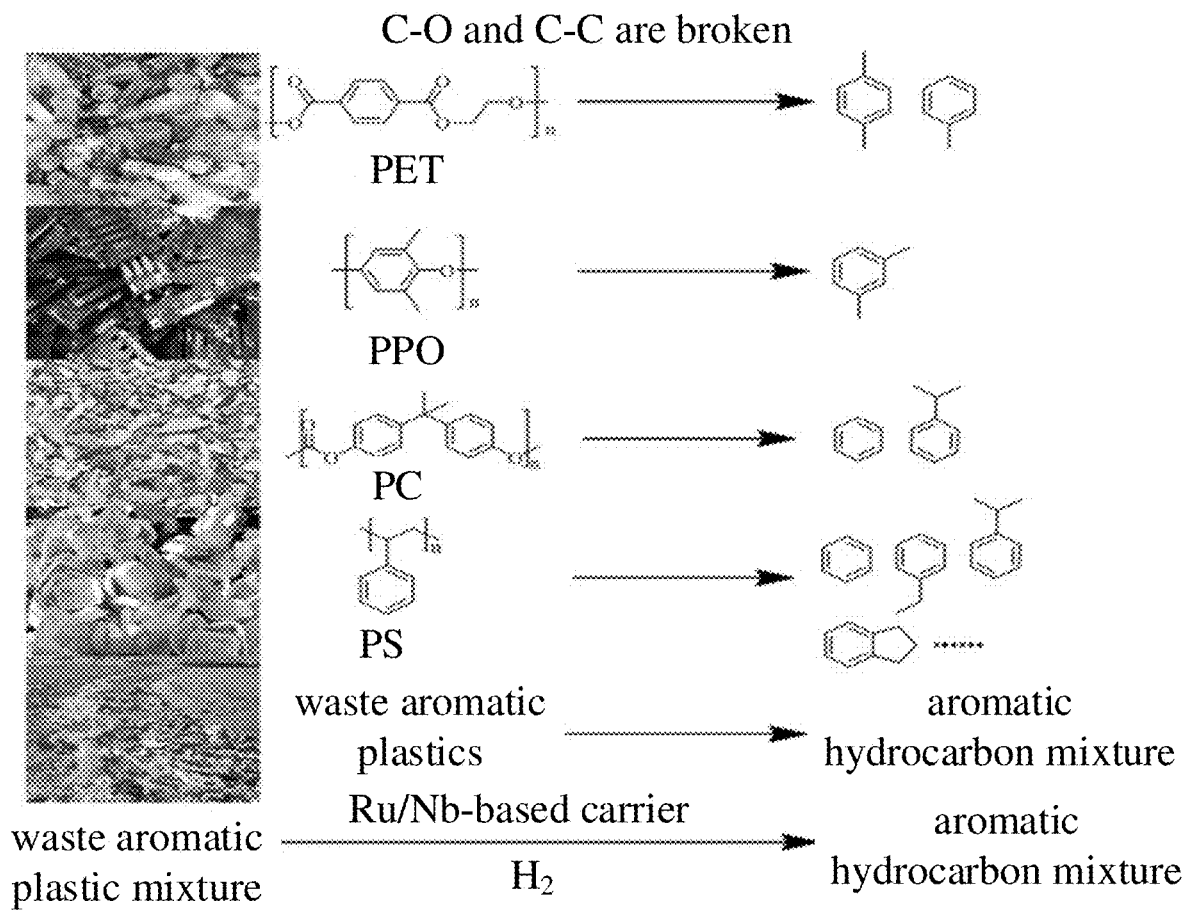
FIG. 2 is a schematic diagram of the preparation of aromatic hydrocarbons by catalytic conversion of aromatic plastic waste according to some examples of the present disclosure.

As shown in FIG. 2, for a single kind of polymer containing aromatic rings and a mixture of various kinds of polymers containing aromatic rings, specific kind of aromatic hydrocarbon can be prepared.

P-xylene, toluene and benzene, in which p-xylene is the main product, can be prepared by catalytic hydrocracking of polyethylene terephthalate (PET)-based through the method of the present disclosure.

M-xylene can be prepared by catalytic hydrocracking of polyphenylene oxide (PPO)-based through the method of the present disclosure.

Benzene and cumene can be prepared by hydrocracking of polycarbonate (PC)-based through the method of the present disclosure.

Benzene, ethylbenzene, cumene and tetrahydroindene-based can be prepared by hydrocracking of polystyrene (PS)-based through the method of the present disclosure.

Through the method of the present disclosure, the widely distributed, cheap and easily available waste plastics can be used as raw materials, and the C—O and C—C linkage bonds can be selectively broken through the catalytic effect of the catalyst, and the hydrogenation of the aromatic ring can be avoided at the same time, and the aromatic hydrocarbon-based compounds can be prepared with high yield. The catalytic system can convert single plastic to selectively produce target chemicals, such as from polyethylene terephthalate-based to p-xylene, from polyphenylene oxide-based to o-xylene, and important bulk chemicals can be obtained. More importantly, this method can also convert mixed plastics into aromatic hydrocarbon mixtures, such as mineral water bottles and other domestic plastic products. It is of great significance for catalytic conversion of waste plastics to aromatic hydrocarbons, which can greatly save energy, reduce environmental pollution and facilitate industrial application.

Example 1

Test materials: polymer containing aromatic rings: polyethylene terephthalate, mass of polymer containing aromatic rings: 0.1 g; solvent: water, mass of solvent: 10 g; concentration of substrate: 1%;

Catalyst: active ingredient is Ru, carrier is $Nb_2O_5$, and mass of catalyst is 0.1 g;

Experimental conditions: hydrogen pressure: 0.3 MPa; reaction temperature: 200° C.; reaction time: 10 h;

Test method: 0.1 g polyethylene terephthalate was crushed to 10 mm in a grinder, and the broken polyethylene terephthalate was dispersed in 10 g of water. Then, the dispersion and 0.1 g of $Ru/Nb_2O_5$ was respectively put into a stainless steel high-pressure reactor with PTFE liner, then the stainless steel high-pressure reactor was sealed and filled with 0.3 MPa hydrogen, heated to the required temperature of 200° C. under rapid stirring, and the reaction was stopped after reacting for 10 hours, cooling, centrifuging the catalyst, and the supernatant was distilled in an order from low boiling point to high boiling point to obtain toluene with 23% molar yield of aromatic hydrocarbons and p-xylene with 62% molar yield of aromatic hydrocarbons, respectively.

Example 2

The difference from Example 1 is that the active ingredient in the catalyst is Fe.

Example 3

The difference from Example 1 is that the active ingredient in the catalyst is Co.

Example 4

The difference from Example 1 is that the active ingredient in the catalyst is Ni.

Example 5

The difference from Example 1 is that the active ingredient in the catalyst is Cu.

Example 6

The difference from Example 1 is that the carrier in the catalyst is $Nb_2O_5$—$Al_2O_3$.

Example 7

The difference from Example 1 is that the carrier in the catalyst is Nb-SBA-15.

Example 8

The difference from Example 1 is that the carrier in the catalyst is $NbOPO_4$.

Example 9

The difference from Example 1 is that the carrier in the catalyst is $Nb_2O_5$—$SiO_2$.

Example 10

The difference from Example 1 is that the carrier in the catalyst is $TiO_2$.

Example 11

The difference from Example 1 is that the carrier in the catalyst is $ZrO_2$.

Example 12

The difference from Example 1 is that the carrier in the catalyst is HZSM-5.

Example 13

The difference from Example 1 is that the carrier in the catalyst is $Al_2O_3$.

Example 14

The difference from Example 1 is that the carrier in the catalyst is $CeO_2$.

Example 15

The difference from Example 1 is that the mass of the polymer containing aromatic rings is 0.3 g;

Solvent: octane, mass of solvent: 10 g; concentration of substrate: 3%;

Hydrogen pressure: 0.5 MPa; reaction temperature: 300° C.; reaction time: 16 h.

Example 16

The difference from Example 15 is that the polymer containing aromatic rings is polyphenylene oxide.

Example 17

The difference from Example 15 is that the polymer containing aromatic rings is polycarbonate.

Example 18

The difference from Example 15 is that the polymer containing aromatic rings is polystyrene.

Example 19

The difference from Example 15 is that the polymer containing aromatic rings is polysulfone.

Example 20

The difference from Example 15 is that the polymer containing aromatic rings is polyphenylene sulfide.

Example 21

The difference from Example 15 is that the polymer containing aromatic rings is polyphenylacetylene.

Example 22

The difference from Example 15 is that the polymer containing aromatic rings is a Sprite bottle.

Example 23

The difference from Example 15 is that the polymer containing aromatic rings is a Nestle coffee bottle.

Example 24

The difference from Example 15 is that the polymer containing aromatic rings is a waste PC board.

Example 25

The difference from Example 15 is that the polymer containing aromatic rings is a waste fast food box.

Example 26

The difference from Example 15 is that the solvent is hexane.

Example 27

The difference from Example 15 is that the solvent is dodecane.

Example 28

The difference from Example 15 is that the solvent is water.

Example 29

The difference from Example 15 is that the polymer containing aromatic rings is polyphenylene oxide and polyethylene terephthalate.

Example 30

The difference from Example 15 is that the polymer containing aromatic rings is polyphenylene oxide and polycarbonate.

Example 31

The difference from Example 15 is that the polymer containing aromatic rings is a waste Sprite bottle and a waste fast food box.

Example 32

The difference from Example 15 is that the mass of the polymer containing aromatic rings is 0.1 g and the concentration of the substrate is 1%.

Example 33

The difference from Example 15 is that the reaction temperature is 280° C.

Example 34

The difference from Example 15 is that the reaction temperature is 320° C.

Example 35

The difference from Example 15 is that the hydrogen pressure is 1.0 MPa.

Example 36

The difference from Example 15 is that the reaction time is 5 h.

Example 37

The difference from Example 1 is that the polymer containing aromatic rings is a mixture of polyethylene terephthalate and polystyrene, and the solvent is dodecane; Reaction temperature: 300° C., reaction time: 10 h.

Example 38

The difference from Example 6 is that the active ingredient in the catalyst is Pd.

Example 39

The difference from Example 7 is that the active ingredient in the catalyst is Pd.

Example 40

The difference from Example 8 is that the active ingredient in the catalyst is Pd.

Example 41

The difference from Example 9 is that the active ingredient in the catalyst is Pd.

Example 42

The difference from Example 10 is that the active ingredient in the catalyst is Pd.

Example 43

The difference from Example 1 is that the active ingredient in the catalyst is Pd.

Example 44

The difference from Example 6 is that the active ingredient in the catalyst is Pt.

Example 45

The difference from Example 7 is that the active ingredient in the catalyst is Pt.

Example 46

The difference from Example 8 is that the active ingredient in the catalyst is Pt.

Example 47

The difference from Example 9 is that the active ingredient in the catalyst is Pt.

Example 48

The difference from Example 1 is that the active ingredient in the catalyst is Pt.

Example 49

The difference from Example 13 is that the active ingredient in the catalyst is Pt.

Example 50

The difference from Example 14 is that the active ingredient in the catalyst is Pt.

Example 51

The difference from Example 6 is that the active ingredient in the catalyst is Rh.

Example 52

The difference from Example 7 is that the active ingredient in the catalyst is Rh.

Example 53

The difference from Example 8 is that the active ingredient in the catalyst is Rh.

Example 54

The difference from Example 9 is that the active ingredient in the catalyst is Rh.

Example 55

The difference from Example 1 is that the active ingredient in the catalyst is Rh.

Example 56

The difference from Example 13 is that the active ingredient in the catalyst is Rh.

Example 57

The difference from Example 14 is that the active ingredient in the catalyst is Rh.

Example 58

The difference from Example 6 is that the active ingredient in the catalyst is Ni.

Example 59

The difference from Example 7 is that the active ingredient in the catalyst is Ni.

Example 60

The difference from Example 8 is that the active ingredient in the catalyst is Ni.

Example 61

The difference from Example 9 is that the active ingredient in the catalyst is Ni.

Example 62

The difference from Example 6 is that the active ingredient in the catalyst is Fe.

Example 63

The difference from Example 7 is that the active ingredient in the catalyst is Fe.

Example 64

The difference from Example 8 is that the active ingredient in the catalyst is Fe.

Example 65

The difference from Example 9 is that the active ingredient in the catalyst is Fe.

Example 66

The difference from Example 6 is that the active ingredient in the catalyst is Co.

Example 67

The difference from Example 7 is that the active ingredient in the catalyst is Co.

Example 68

The difference from Example 8 is that the active ingredient in the catalyst is Co.

Example 69

The difference from Example 9 is that the active ingredient in the catalyst is Co.

Example 70

The difference from Example 6 is that the active ingredient in the catalyst is Cu.

Example 71

The difference from Example 7 is that the active ingredient in the catalyst is Cu.

Example 72

The difference from Example 8 is that the active ingredient in the catalyst is Cu.

Example 73

The difference from Example 9 is that the active ingredient in the catalyst is Cu.

Example 74

The difference from Example 1 is that the active ingredient in the catalyst is Pd.

Example 75

The difference from Example 1 is that the active ingredient in the catalyst is Pt.

Example 76

The difference from Example 1 is that the active ingredient in the catalyst is Rh.

Comparative Example 1

The difference from Example 1 is that in the catalyst, HZSM-5 is used instead of Ru/Nb$_2$O$_5$ and nitrogen is used instead of hydrogen.

Comparative Example 2

The difference from Example 1 is that in the catalyst, HZSM-5 is used instead of Ru/Nb$_2$O$_5$.

Comparative Example 3

The difference from Example 37 is that in the catalyst, HZSM-5 is used instead of Nb$_2$O$_5$.

Comparative Example 4

The difference from Example 37 is that in the catalyst, HZSM-5 is used instead of Ru/Nb$_2$O$_5$, and water is used as solvent instead of dodecane.

Comparative Example 5

The difference from Example 1 is that the active ingredient in the catalyst is Ag.

Comparative Example 6

The difference from Example 1 is that the active ingredient in the catalyst is Au.

Comparative Example 7

The difference from Example 1 is that the active ingredient in the catalyst is V.

Comparative Example 8

The difference from Example 1 is that the active ingredient in the catalyst is Cr.

Comparative Example 9

The difference from Example 1 is that the active ingredient in the catalyst is Mn.

Comparative Example 10

The difference from Example 6 is that the active ingredient in the catalyst is Ag.

Comparative Example 11

The difference from Example 6 is that the active ingredient in the catalyst is Au.

Comparative Example 12

The difference from Example 6 is that the active ingredient in the catalyst is V.

Comparative Example 13

The difference from Example 6 is that the active ingredient in the catalyst is Cr.

Comparative Example 14

The difference from Example 6 is that the active ingredient in the catalyst is Mn.

Comparative Example 15

The difference from Example 7 is that the active ingredient in the catalyst is Ag.

Comparative Example 16

The difference from Example 7 is that the active ingredient in the catalyst is Au.

Comparative Example to 17

The difference from Example 7 is that the active ingredient in the catalyst is V.

Comparative Example 18

The difference from Example 7 is that the active ingredient in the catalyst is Cr.

Comparative Example 19

The difference from Example 7 is that the active ingredient in the catalyst is Mn.

Comparative Example 20

The difference from Example 9 is that the active ingredient in the catalyst is Ag.

Comparative Example 21

The difference from Example 9 is that the active ingredient in the catalyst is Au.

Comparative Example 22

The difference from Example 9 is that the active ingredient in the catalyst is V.

Comparative Example 23

The difference from Example 9 is that the active ingredient in the catalyst is Cr.

Comparative Example 24

The difference from Example 9 is that the active ingredient in the catalyst is Mn.

The results of the molar yields of the aromatic hydrocarbons of the above Examples 1 to 76 and Comparative Examples of 1 to 24 are shown in Table 1.

TABLE 1

Molar yields of aromatic hydrocarbons prepared by catalytic cracking of polymers containing different aromatic rings with different catalysts

| Test cases |  |  |  |  |  |  |  | Other aromatic hydrocarbons | Molar yield of aromatic hydrocarbons % |
|---|---|---|---|---|---|---|---|---|---|
| Example 1  | 0  | 20 | 62 | 0  | 0  | 0  | 0 | 2 | 84 |
| Example 2  | 0  | 19 | 16 | 0  | 0  | 0  | 0 | 0 | 35 |
| Example 3  | 0  | 14 | 15 | 0  | 0  | 0  | 0 | 4 | 33 |
| Example 4  | 0  | 12 | 16 | 0  | 0  | 0  | 0 | 3 | 31 |
| Example 5  | 0  | 16 | 13 | 0  | 0  | 0  | 0 | 2 | 31 |
| Example 6  | 0  | 29 | 56 | 0  | 0  | 0  | 0 | 0 | 85 |
| Example 7  | 0  | 28 | 54 | 0  | 0  | 0  | 0 | 0 | 84 |
| Example 8  | 0  | 22 | 60 | 0  | 0  | 0  | 0 | 3 | 85 |
| Example 9  | 0  | 25 | 51 | 0  | 0  | 0  | 0 | 1 | 77 |
| Example 10 | 0  | 19 | 17 | 0  | 0  | 0  | 0 | 0 | 36 |
| Example 11 | 0  | 21 | 14 | 0  | 0  | 0  | 0 | 2 | 37 |
| Example 12 | 0  | 26 | 12 | 0  | 0  | 0  | 0 | 0 | 52 |
| Example 13 | 0  | 15 | 18 | 0  | 0  | 0  | 0 | 1 | 34 |
| Example 14 | 0  | 22 | 18 | 0  | 0  | 0  | 0 | 1 | 41 |
| Example 15 | 21 | 37 | 25 | 0  | 0  | 0  | 0 | 0 | 83 |
| Example 16 | 0  | 0  | 0  | 85 | 0  | 0  | 0 | 0 | 85 |
| Example 17 | 57 | 1  | 0  | 0  | 0  | 16 | 0 | 1 | 75 |
| Example 18 | 50 | 1  | 0  | 0  | 7  | 6  | 5 | 4 | 73 |
| Example 19 | 46 | 0  | 0  | 0  | 0  | 15 | 0 | 2 | 63 |
| Example 20 | 51 | 0  | 0  | 0  | 0  | 0  | 0 | 0 | 51 |
| Example 21 | 38 | 2  | 0  | 0  | 12 | 3  | 2 | 4 | 61 |
| Example 22 | 19 | 33 | 24 | 0  | 0  | 0  | 0 | 0 | 76 |
| Example 23 | 18 | 34 | 23 | 0  | 0  | 0  | 0 | 0 | 75 |
| Example 24 | 52 | 1  | 0  | 0  | 0  | 14 | 0 | 1 | 68 |
| Example 25 | 48 | 1  | 0  | 0  | 8  | 6  | 4 | 3 | 70 |
| Example 26 | 20 | 35 | 24 | 0  | 0  | 0  | 0 | 0 | 79 |
| Example 27 | 19 | 39 | 20 | 0  | 0  | 0  | 0 | 0 | 78 |
| Example 28 | 16 | 34 | 30 | 0  | 0  | 0  | 0 | 0 | 80 |
| Example 29 | 14 | 12 | 15 | 41 | 0  | 0  | 0 | 0 | 82 |
| Example 30 | 25 | 1  | 0  | 39 | 0  | 8  | 0 | 0 | 73 |
| Example 31 | 42 | 9  | 11 | 0  | 4  | 3  | 5 | 3 | 77 |
| Example 32 | 22 | 37 | 27 | 0  | 0  | 0  | 0 | 0 | 85 |
| Example 33 | 15 | 26 | 43 | 0  | 0  | 0  | 0 | 0 | 84 |
| Example 34 | 38 | 30 | 11 | 0  | 0  | 0  | 0 | 0 | 79 |
| Example 35 | 7  | 24 | 26 | 0  | 0  | 0  | 0 | 0 | 57 |
| Example 36 | 9  | 21 | 18 | 0  | 0  | 0  | 0 | 0 | 48 |
| Example 37 | 31 | 14 | 15 | 0  | 9  | 1  | 4 | 2 | 76 |
| Example 38 | 8  | 25 | 35 | 0  | 0  | 0  | 0 | 0 | 68 |
| Example 39 | 8  | 22 | 34 | 0  | 0  | 0  | 0 | 0 | 63 |
| Example 40 | 6  | 21 | 33 | 0  | 0  | 0  | 0 | 0 | 60 |
| Example 41 | 4  | 13 | 31 | 0  | 0  | 0  | 0 | 0 | 48 |
| Example 42 | 6  | 7  | 17 | 0  | 0  | 0  | 0 | 0 | 30 |
| Example 43 | 10 | 18 | 22 | 0  | 0  | 0  | 0 | 1 | 51 |
| Example 44 | 6  | 24 | 36 | 0  | 0  | 0  | 0 | 0 | 66 |
| Example 45 | 8  | 21 | 32 | 0  | 0  | 0  | 0 | 0 | 61 |
| Example 46 | 7  | 22 | 29 | 0  | 0  | 0  | 0 | 0 | 58 |
| Example 47 | 4  | 16 | 35 | 0  | 0  | 0  | 0 | 0 | 55 |
| Example 48 | 9  | 19 | 25 | 0  | 0  | 1  | 0 | 0 | 54 |
| Example 49 | 2  | 11 | 19 | 0  | 0  | 0  | 0 | 1 | 32 |
| Example 50 | 5  | 9  | 21 | 0  | 0  | 0  | 0 | 1 | 35 |
| Example 51 | 7  | 28 | 31 | 0  | 0  | 0  | 0 | 0 | 66 |
| Example 52 | 4  | 22 | 31 | 0  | 0  | 0  | 0 | 2 | 59 |
| Example 53 | 7  | 21 | 24 | 0  | 0  | 0  | 0 | 2 | 54 |
| Example 54 | 3  | 21 | 32 | 0  | 0  | 0  | 0 | 0 | 56 |
| Example 55 | 11 | 23 | 24 | 0  | 0  | 0  | 0 | 1 | 59 |

TABLE 1-continued

Molar yields of aromatic hydrocarbons prepared by catalytic cracking of
polymers containing different aromatic rings with different catalysts Distribution of molar yield of aromatic hydrocarbons

| Test cases | benzene | toluene | p-xylene | m-xylene | ethylbenzene | cumene | indane | Other aromatic hydrocarbons | Molar yield of aromatic hydrocarbons % |
|---|---|---|---|---|---|---|---|---|---|
| Example 56 | 1 | 9 | 22 | 0 | 0 | 0 | 0 | 1 | 33 |
| Example 57 | 4 | 11 | 18 | 0 | 0 | 0 | 0 | 1 | 33 |
| Example 58 | 14 | 11 | 15 | 0 | 0 | 0 | 0 | 0 | 40 |
| Example 59 | 13 | 11 | 13 | 0 | 0 | 0 | 0 | 0 | 37 |
| Example 60 | 14 | 10 | 14 | 0 | 0 | 0 | 0 | 0 | 38 |
| Example 61 | 11 | 14 | 12 | 0 | 0 | 0 | 0 | 0 | 37 |
| Example 62 | 9 | 11 | 14 | 0 | 0 | 0 | 0 | 0 | 34 |
| Example 63 | 13 | 12 | 11 | 0 | 0 | 0 | 0 | 0 | 36 |
| Example 64 | 17 | 10 | 8 | 0 | 0 | 0 | 0 | 0 | 35 |
| Example 65 | 12 | 6 | 12 | 0 | 0 | 0 | 0 | 0 | 30 |
| Example 66 | 9 | 14 | 6 | 0 | 0 | 0 | 0 | 1 | 30 |
| Example 67 | 8 | 11 | 12 | 0 | 0 | 0 | 0 | 0 | 31 |
| Example 68 | 16 | 10 | 5 | 0 | 0 | 0 | 0 | 0 | 31 |
| Example 69 | 12 | 8 | 7 | 0 | 0 | 0 | 0 | 0 | 37 |
| Example 70 | 11 | 7 | 11 | 0 | 0 | 0 | 0 | 0 | 29 |
| Example 71 | 10 | 11 | 10 | 0 | 0 | 0 | 0 | 0 | 31 |
| Example 72 | 15 | 6 | 8 | 0 | 0 | 0 | 0 | 0 | 29 |
| Example 73 | 11 | 11 | 17 | 0 | 0 | 0 | 0 | 0 | 39 |
| Example 74 | 14 | 11 | 15 | 0 | 0 | 0 | 0 | 0 | 40 |
| Example 75 | 13 | 11 | 13 | 0 | 0 | 0 | 0 | 0 | 37 |
| Example 76 | 14 | 10 | 14 | 0 | 0 | 0 | 0 | 0 | 38 |
| Comparative Example 1 | 0 | 0 | 0 | 0 | 0 | 0 | 0 | 0 | 0 |
| Comparative Example 2 | 0 | 0 | 0 | 0 | 0 | 0 | 0 | 0 | 0 |
| Comparative Example 3 | 5 | 8 | 11 | 0 | 0 | 0 | 0 | 1 | 24 |
| Comparative Example 4 | 1 | 3 | 5 | 0 | 0 | 0 | 0 | 0 | 9 |
| Comparative Example 5 | 2 | 7 | 124 | 0 | 0 | 0 | 0 | 3 | 23 |
| Comparative Example 6 | 2 | 8 | 10 | 0 | 0 | 0 | 0 | 2 | 20 |
| Comparative Example 7 | 4 | 11 | 12 | 0 | 0 | 0 | 0 | 2 | 27 |
| Comparative Example 8 | 3 | 6 | 11 | 0 | 0 | 0 | 0 | 1 | 21 |
| Comparative Example 9 | 2 | 3 | 6 | 0 | 0 | 0 | 0 | 0 | 11 |
| Comparative Example 10 | 0 | 2 | 4 | 0 | 0 | 0 | 0 | 1 | 7 |
| Comparative Example 11 | 0 | 1 | 2 | 0 | 0 | 0 | 0 | 1 | 4 |
| Comparative Example 12 | 2 | 4 | 15 | 0 | 0 | 0 | 0 | 0 | 21 |
| Comparative Example 13 | 2 | 6 | 10 | 0 | 0 | 0 | 0 | 1 | 19 |
| Comparative Example 14 | 2 | 4 | 5 | 0 | 0 | 0 | 0 | 1 | 12 |
| Comparative Example 15 | 3 | 6 | 11 | 0 | 0 | 0 | 0 | 0 | 20 |
| Comparative Example 16 | 1 | 5 | 9 | 0 | 0 | 0 | 0 | 1 | 16 |
| Comparative Example 17 | 3 | 4 | 9 | 0 | 0 | 0 | 0 | 0 | 16 |
| Comparative Example 18 | 4 | 7 | 4 | 0 | 0 | 0 | 0 | 0 | 15 |
| Comparative Example 19 | 1 | 2 | 2 | 0 | 0 | 0 | 0 | 0 | 5 |
| Comparative Example 20 | 0 | 2 | 4 | 0 | 0 | 0 | 0 | 0 | 6 |
| Comparative Example 21 | 2 | 7 | 17 | 0 | 0 | 0 | 0 | 2 | 28 |
| Comparative Example 22 | 3 | 7 | 10 | 0 | 0 | 0 | 0 | 1 | 21 |

TABLE 1-continued

Molar yields of aromatic hydrocarbons prepared by catalytic cracking of polymers containing different aromatic rings with different catalysts

| Test cases | 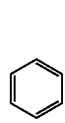 | 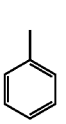 | 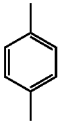 | 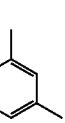 | 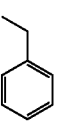 | 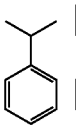 | 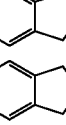 | Other aromatic hydrocarbons | Molar yield of aromatic hydrocarbons % |
|---|---|---|---|---|---|---|---|---|---|
| Comparative Example 23 | 3 | 2 | 6 | 0 | 0 | 0 | 0 | 3 | 14 |
| Comparative Example 24 | 2 | 5 | 6 | 0 | 0 | 0 | 0 | 2 | 15 |

As can be known from the above Table, when the polymer containing aromatic rings is at least one of polyethylene terephthalate, polycarbonate, polyphenylene oxide and polystyrene, the active ingredient in the catalyst is Ru, and the carrier is at least one selected from HZSM-5, $Nb_2O_5$, $Nb_2O_5$—$Al_2O_3$, Nb-SBA-15, $Nb_2O_5$—$SiO_2$ or $NbOPO_4$, the total molar yield of the aromatic hydrocarbons is as high as 37% or more, and the aromatic hydrocarbons can be at least one selected from benzene, toluene, ethylbenzene, p-xylene, m-xylene, cumene, indene and substituted indene. The total molar yields of the aromatic hydrocarbons in Examples are higher than that in Comparative Examples in which the active ingredients in the catalyst are Ag and Au respectively, and the carrier is $Nb_2O_5$.

When the polymer containing aromatic rings is at least one of polyethylene terephthalate, polycarbonate, polyphenylene oxide and polystyrene, the active ingredient in the catalyst is Ru, and the carrier is at least one selected from HZSM-5, $Nb_2O_5$, $Nb_2O_5$—$Al_2O_3$, Nb-SBA-15, $Nb_2O_5$—$SiO_2$ or $NbOPO_4$, the total molar yield of the aromatic hydrocarbons is as high as 52% or more, and the aromatic hydrocarbons can be at least one selected from benzene, toluene, ethylbenzene, p-xylene, m-xylene, cumene, indene and substituted indene.

When the polymer containing aromatic rings is at least one of polyethylene terephthalate, polycarbonate, polyphenylene oxide and polystyrene, the active ingredient in the catalyst is Ru, and the carrier is $Nb_2O_5$, $Nb_2O_5$—$Al_2O_3$, Nb-SBA-15, $Nb_2O_5$—$SiO_2$ or $NbOPO_4$, the total molar yield of the aromatic hydrocarbons is as high as 75% or more, and the aromatic hydrocarbons can be at least one selected from benzene, toluene, ethylbenzene, p-xylene, m-xylene, cumene, indene and substituted indene.

According to some examples of the present disclosure, when the polymer containing aromatic rings is at least one of polyethylene terephthalate and polyphenylene oxide, the active ingredient in the catalyst is Ru and the carrier is $Nb_2O_5$, $Nb_2O_5$—$Al_2O_3$, Nb-SBA-15 or $NbOPO_4$, the total molar yield of the aromatic hydrocarbons is as high as 80% or more, and the aromatic hydrocarbons can be at least one selected from benzene, toluene, p-xylene and m-xylene.

Further, when the polymer containing aromatic rings is polyethylene terephthalate or polyphenylene oxide, the active ingredient in the catalyst is Ru and the carrier is $Nb_2O_5$, $Nb_2O_5$—$Al_2O_3$ or $NbOPO_4$, the total molar yield of the aromatic hydrocarbons is as high as 84% or more, and the aromatic hydrocarbons can be at least one selected from benzene, toluene and p-xylene.

Further, when the polymer containing aromatic rings is polyethylene terephthalate, the active ingredient in the catalyst is Ru and the carrier is $Nb_2O_5$, $Nb_2O_5$—$Al_2O_3$ or $NbOPO_4$, the C—O and C=O bonds can be selectively broken to obtain bulk chemicals p-xylene, and the molar yield thereof is 56%-62%.

When the polymer containing aromatic rings is polyethylene terephthalate, the active ingredient in the catalyst is Ru and the carrier is $Nb_2O_5$, the molar yield of p-xylene is 62%.

Further, according to some examples of the present disclosure, the catalyst is Ru supported on $Nb_2O_5$ carrier, the polymer containing aromatic rings is polyphenylene oxide, the C—O bond can be selectively broke to obtain bulk chemicals m-xylene, and the molar yield thereof is as high as 85%.

According to some examples of the present disclosure, when the polymer containing aromatic rings is polystyrene, the active ingredient in the catalyst is Ru and the carrier is $Nb_2O_5$, the C—C bond connected with the benzene ring can be selectively broke, and the molar yield of the aromatic hydrocarbons is as high as 73%, and the conversion of polystyrene is relatively thorough, and the bulk chemicals benzene is obtained, and the molar yield thereof is as high as 50%. Therefore, the method of the present disclosure can greatly improve the recovery efficiency of polystyrene which is difficult to be treated in industry.

According to some examples of the present disclosure, when the polymer containing aromatic rings is polycarbonate, the active ingredient in the catalyst is Ru, and the carrier is $Nb_2O_5$, the C—O bond and the C—C bond connected with the benzene ring can be selectively broke to obtain bulk chemicals benzene, and the molar yield thereof is as high as 57%. Therefore, the method of the present disclosure can greatly improve the recovery efficiency of polycarbonate which is difficult to be treated in industry, the conversion of polycarbonate is relatively thorough, the molar yield of the aromatic hydrocarbons is as high as 75%, greatly improving the conversion efficiency of polycarbonate, and the obtained aromatic hydrocarbons are easy to be separated.

When the polymer containing aromatic rings is at least one of polyethylene terephthalate, polycarbonate, polyphenylene oxide and polystyrene, the active ingredient in the catalyst is Pd, and the carrier is at least one selected from $Nb_2O_5$, $Nb_2O_5$—$Al_2O_3$, Nb-SBA-15, $Nb_2O_5$—$SiO_2$ or $NbOPO_4$, the total molar yield of the aromatic hydrocarbons is higher than 48%, and the yield of p-xylene is higher than 31%. According to some examples of the present disclosure, when the carriers are Nb-SBA-15, $Nb_2O_5$—$Al_2O_3$ and NbOPO$_4$, the total molar yield of the aromatic hydrocarbons is higher than 60%. According to some examples of the present disclosure, the total molar yield of the aromatic hydrocarbons is as high as 68% when the carrier is Nb$_2$O$_5$—Al$_2$O$_3$. The total molar yields of the aromatic hydrocarbons in Examples are higher than that in Comparative Examples in which the active ingredients in the catalyst are Ag, Au, V, Cr and Mn respectively, and the carrier is Nb$_2$O$_5$—Al$_2$O$_3$.

When the polymer containing aromatic rings is at least one of polyethylene terephthalate, polycarbonate, polyphenylene oxide and polystyrene, the active ingredient in the catalyst is Pt, and the carrier is at least one selected from Al$_2$O$_3$, CeO$_2$, Nb$_2$O$_5$, Nb$_2$O$_5$—Al$_2$O$_3$, Nb-SBA-15, Nb$_2$O$_5$—SiO$_2$ and NbOPO$_4$, the total molar yield of the aromatic hydrocarbons is higher than 32%. The carrier is at least one selected from Nb$_2$O$_5$, Nb$_2$O$_5$—Al$_2$O$_3$, Nb-SBA-15, Nb$_2$O$_5$—SiO$_2$ or NbOPO$_4$, and the total molar yield of the aromatic hydrocarbons is higher than 54%. When the carrier is selected from Nb$_2$O$_5$—Al$_2$O$_3$ and Nb-SBA-15, the total molar yield of the aromatic hydrocarbons is higher than 61%, and the yield of p-xylene is higher than 32%. When the carrier is Nb$_2$O$_5$—Al$_2$O$_3$, the total molar yield of the aromatic hydrocarbons is 66%, and the yield of p-xylene is higher than 36%. The total molar yields of the aromatic hydrocarbons in Examples are higher than that in Comparative Examples in which the active ingredients in the catalyst are Ag, Au, V, Cr and Mn respectively, and the carrier is Nb$_2$O$_5$—Al$_2$O$_3$.

When the polymer containing aromatic rings is at least one of polyethylene terephthalate, polycarbonate, polyphenylene oxide and polystyrene, the active ingredient in the catalyst is Rh, and the carrier is at least one selected from Al$_2$O$_3$, CeO$_2$, Nb$_2$O$_5$, Nb$_2$O$_5$—Al$_2$O$_3$, Nb-SBA-15, Nb$_2$O$_5$—SiO$_2$ and NbOPO$_4$, the total molar yield of the aromatic hydrocarbons is higher than 33%. When the carrier is at least one selected from Nb$_2$O$_5$, Nb$_2$O$_5$—Al$_2$O$_3$, Nb-SBA-15 and Nb$_2$O$_5$—SiO$_2$, the total molar yield of the aromatic hydrocarbons is higher than 55%. When the carrier is Nb$_2$O$_5$—Al$_2$O$_3$, the highest yield is obtained, the total molar yield of the aromatic hydrocarbons is as high as 66%, and the yield of p-xylene is as high as 31%. The total molar yields of the aromatic hydrocarbons in Examples are higher than that in Comparative Examples in which the active ingredients in the catalyst are Ag, Au, V, Cr and Mn respectively, and the carrier is Nb$_2$O$_5$—Al$_2$O$_3$.

When the polymer containing aromatic rings is at least one of polyethylene terephthalate, polycarbonate, polyphenylene oxide and polystyrene, the active ingredient in the catalyst is Ni, and the carrier is at least one selected from Nb$_2$O$_5$, Nb$_2$O$_5$—Al$_2$O$_3$, Nb-SBA-15, Nb$_2$O$_5$—SiO$_2$ or NbOPO$_4$, the total molar yield of the aromatic hydrocarbons is higher than 30%. When the carrier is Nb$_2$O$_5$—Al$_2$O$_3$, the highest yield is obtained. The total molar yields of the aromatic hydrocarbons in Examples are higher than that in Comparative Examples in which the active ingredients in the catalyst are Ag, Au, V, Cr and Mn respectively, and the carrier is Nb$_2$O$_5$—Al$_2$O$_3$.

When the polymer containing aromatic rings is at least one of polyethylene terephthalate, polycarbonate, polyphenylene oxide and polystyrene, the active ingredient in the catalyst is Fe, and the carrier is at least one selected from Nb$_2$O$_5$, Nb$_2$O$_5$—Al$_2$O$_3$, Nb-SBA-15, Nb$_2$O$_5$—SiO$_2$ or NbOPO$_4$, the total molar yield of the aromatic hydrocarbons is higher than 30%. When the carrier is Nb-SBA-15, the highest yield is obtained. The total molar yields of the aromatic hydrocarbons in Examples are higher than that in Comparative Examples in which the active ingredients in the catalyst are Ag, Au, V, Cr and Mn respectively, and the carrier is Nb-SBA-15.

When the polymer containing aromatic rings is at least one of polyethylene terephthalate, polycarbonate, polyphenylene oxide and polystyrene, the active ingredient in the catalyst is Co, and the carrier is at least one selected from Nb$_2$O$_5$, Nb$_2$O$_5$—Al$_2$O$_3$, Nb-SBA-15, Nb$_2$O$_5$—SiO$_2$ or NbOPO$_4$, and the total molar yield of the aromatic hydrocarbons is higher than 30%. When the carrier is Nb$_2$O$_5$—SiO$_2$, the highest yield is obtained. The total molar yields of the aromatic hydrocarbons in Examples are higher than that in Comparative Examples in which the active ingredients in the catalyst are Ag, Au, V, Cr and Mn respectively, and the carrier is Nb$_2$O$_5$—SiO$_2$.

When the polymer containing aromatic rings is at least one of polyethylene terephthalate, polycarbonate, polyphenylene oxide and polystyrene, the active ingredient in the catalyst is Cu, and the carrier is at least one selected from Nb$_2$O$_5$, Nb$_2$O$_5$—Al$_2$O$_3$, Nb-SBA-15, Nb$_2$O$_5$—SiO$_2$ or NbOPO$_4$, the total molar yield of the aromatic hydrocarbons is higher than 30%. When the carrier is Nb$_2$O$_5$—SiO$_2$, the highest yield is obtained. The total molar yields of the aromatic hydrocarbons in Examples are higher than that in Comparative Examples in which the active ingredients in the catalyst are Ag, Au, V, Cr and Mn respectively, and the carrier is Nb$_2$O$_5$—SiO$_2$.

Those skilled in the art should understand that the discussion of any of the above Examples is only illustrative, and is not intended to imply that the scope of the present disclosure (including the claims) is limited to these Examples; under the idea of the present disclosure, the above Examples or the technical features in different Examples can also be combined, and the steps can be implemented in any order and many other variations of the different aspects of the present disclosure as described above exist and are not provided in detail for the sake of brevity.

Although the present disclosure has been described in combination with specific Examples of the present disclosure, according to the previous description, many substitutions, modifications and variants of these Examples will be obvious to those skilled in the art.

Examples of the present disclosure are intended to cover all such substitutions, modifications and variants falling within the broad scope of the appended claims. Therefore, any omission, modification, equivalent replacement, improvement, etc. made within the spirit and principle of the present disclosure shall be included in the protection scope of the present disclosure.

What is claimed is:

1. A method for preparing aromatic hydrocarbons by hydrocracking a polymer containing aromatic rings, comprising:

reacting the polymer containing aromatic rings dispersed in a solvent with hydrogen under the action of a catalyst at a temperature of no more than 350° C.;

separating a reaction product to obtain the aromatic hydrocarbons; wherein, the catalyst comprises a carrier and an active ingredient supported on the carrier;

the active ingredient comprises Ru;

the carrier comprises at least one of metal oxide, phosphate, molecular sieve, SiO2 or sulfonated carbon;

the metal oxide comprises at least one of Al2O3, Nb2O5, Nb2O5-Al2O3, Nb2O5-SiO2, TiO2, ZrO2, CeO2 or MoO3;

the phosphate comprises at least one of NbOPO4 or ZrOPO4; and the molecule sieve comprises at least one of Nb-SBA-15, Nafion, H-ZSM-5, H-Beta or H-Y.

2. The method according to claim 1, wherein the polymer containing aromatic rings comprises at least one of polyethylene terephthalate, polyphenylene oxide, polycarbonate, polystyrene, polysulfone, polyphenylene sulfide or polyphenylacetylene.

3. The method according to claim 1, wherein the polymer containing aromatic rings comprises at least one of polyethylene terephthalate, polycarbonate, polyphenylene oxide or polystyrene.

4. The method according to claim 3, wherein the active ingredient in the catalyst further comprises at least one of Pt, Pd, Rh, Fe, Ni, Cu or Co.

5. The method according to claim 4, wherein the carrier comprises at least one of H-ZSM-5, ZrO2, CeO2, Nb2O5, Nb2O5-Al2O3, Nb-SBA-15, Nb2O5-SiO2 or NbOPO4.

6. The method according to claim 4, wherein the carrier comprises at least one of Nb2O5, Nb2O5-Al2O3, Nb-SBA-15, Nb2O5-SiO2 and NbOPO4.

* * * * *